(12) United States Patent
Zollinger et al.

(10) Patent No.: US 8,840,577 B1
(45) Date of Patent: Sep. 23, 2014

(54) NEEDLELESS CONNECTOR WITH FLEXIBLE VALVE

(71) Applicants: Christopher J. Zollinger, Chino Hills, CA (US); Jonathan Yeh, Diamond Bar, CA (US); George Michel Mansour, Pomona, CA (US); Matthew Quach, San Gabriel, CA (US)

(72) Inventors: Christopher J. Zollinger, Chino Hills, CA (US); Jonathan Yeh, Diamond Bar, CA (US); George Michel Mansour, Pomona, CA (US); Matthew Quach, San Gabriel, CA (US)

(73) Assignee: Carefusion 303, Inc., San Diego, CA (US)

( * ) Notice: Subject to any disclaimer, the term of this patent is extended or adjusted under 35 U.S.C. 154(b) by 0 days.

(21) Appl. No.: 13/829,227

(22) Filed: Mar. 14, 2013

(51) Int. Cl.
*A61M 37/00* (2006.01)

(52) U.S. Cl.
USPC ............... 604/6.1; 604/167.03; 604/256

(58) Field of Classification Search
CPC .......... A61M 2039/263; A61M 39/26; A61M 2039/2433; A61M 2039/268
USPC ............ 604/6.1, 9.34, 167.03, 237, 247, 256; 251/85
See application file for complete search history.

(56) References Cited

U.S. PATENT DOCUMENTS

| 4,911,403 | A  | * | 3/1990  | Lockwood, Jr. ............... 251/83 |
| 5,730,418 | A  |   | 3/1998  | Feith et al. |
| 5,782,816 | A  |   | 7/1998  | Werschmidt et al. |
| 6,245,048 | B1 | * | 6/2001  | Fangrow et al. ............. 604/249 |
| 6,679,219 | B1 | * | 1/2004  | Pacinelli ................. 123/188.3 |
| 7,184,825 | B2 |   | 2/2007  | Leinsing et al. |
| 2003/0098430 | A1 | * | 5/2003 | Leinsing et al. ........... 251/149.6 |
| 2006/0025724 | A1 |   | 2/2006 | Chen |
| 2006/0027270 | A1 |   | 2/2006 | Truitt et al. |
| 2007/0270756 | A1 |   | 11/2007 | Peppel et al. |
| 2008/0108956 | A1 | * | 5/2008 | Lynn et al. ................. 604/256 |
| 2009/0030401 | A1 | * | 1/2009 | Phillips ................... 604/533 |
| 2011/0028914 | A1 |   | 2/2011 | Mansour et al. |
| 2011/0046573 | A1 | * | 2/2011 | Newton et al. .............. 604/256 |

FOREIGN PATENT DOCUMENTS

| CN | 1139010 A     | 1/1997 |
| WO | 2004/112866 A2 | 12/2004 |
| WO | 2006/078355 A1 | 7/2006 |
| WO | 2011/060384 A1 | 5/2011 |
| WO | 2013/122148 A1 | 8/2013 |

OTHER PUBLICATIONS

International Search Report and Written Opinion mailed on May 8, 2014 for PCT Application No. PCT/US2014/017826 in 10 pages.

* cited by examiner

*Primary Examiner* — Nicholas Lucchesi
*Assistant Examiner* — Gerald Landry, II
(74) *Attorney, Agent, or Firm* — McDermott Will & Emery LLP

(57) ABSTRACT

A flexible valve for a connectors is described. In one example, a flexible valve for a connector includes a head having a top section and a column section defining an axial center of the head, wherein the top section includes a top planar surface that is non-perpendicular with respect to the axial center of the column section; a primary seal portion coupled to the head; and a lower portion coupled to the primary seal portion.

20 Claims, 8 Drawing Sheets

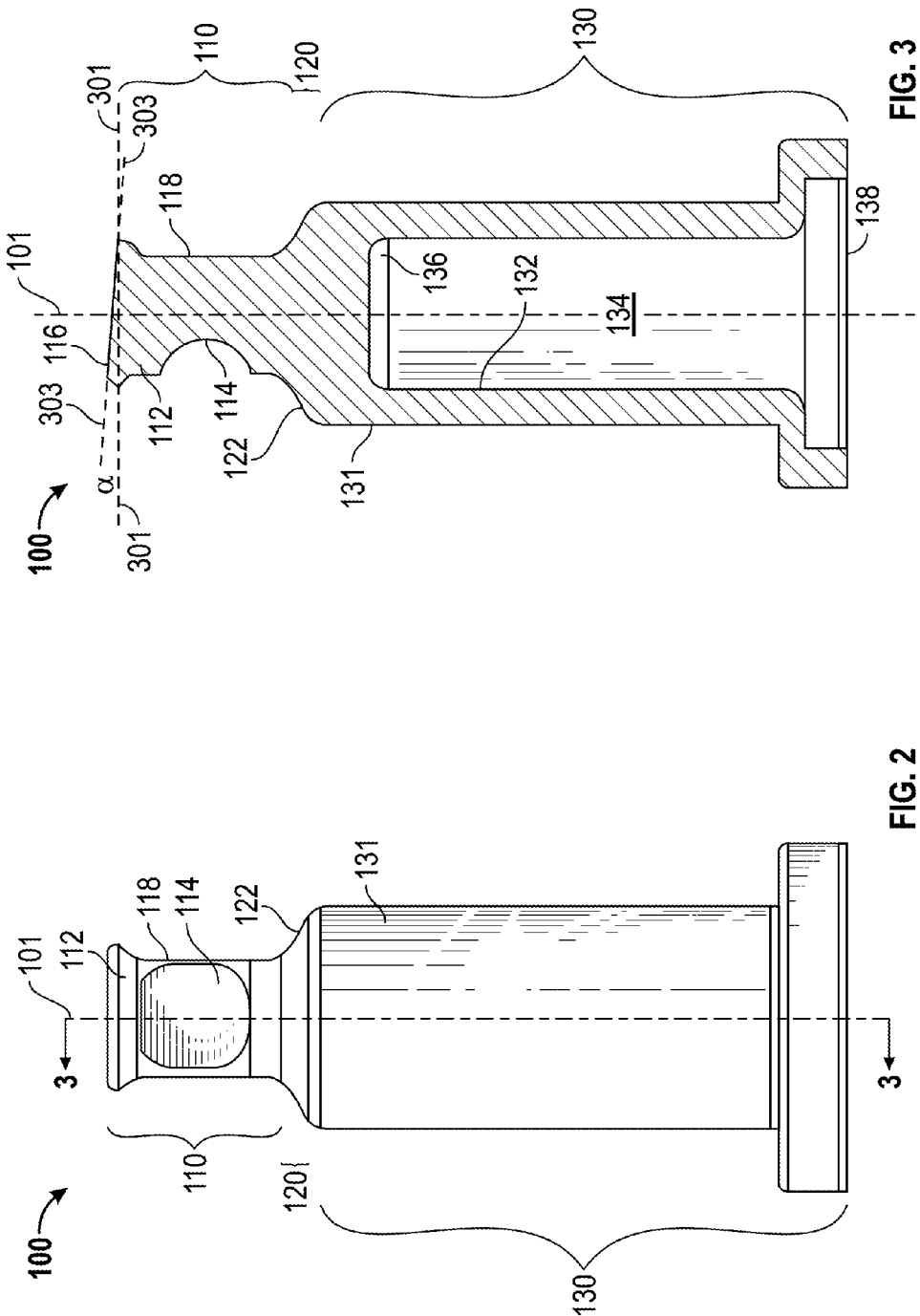

NEEDLELESS CONNECTOR WITH FLEXIBLE VALVE

CROSS-REFERENCES TO RELATED APPLICATIONS

Not applicable.

BACKGROUND

1. Field

The present disclosure relates in general to needleless connectors, and more particularly to, needleless connectors having flexible valves.

2. Description of the Related Art

Medical treatments often include the infusion of a medical fluid (e.g., a saline solution or a liquid medication) to patients using an intravenous (IV) catheter that is connected through an arrangement of flexible tubing and fittings, commonly referred to as an "IV set," to a source of fluid, for example, an IV bag. Certain needleless connectors may be used in an IV set and may have a self-sealing feature to prevent leakage of fluid from an attached tubing when a mating medical implement is decoupled from such a needleless connector. Additionally, a needleless connector may include a mechanical valve for providing the self-sealing feature and controlling the flow of fluid within the IV set.

Certain needleless connectors employ a flexible valve that self-seals by returning to an original position after pressure on the flexible valve is released by a male luer tip when removed from the needleless connector port, for example. However, while certain valves will self-seal along a primary seal when returning to an original position, a portion of the flexible valve proximal to the port opening will typically not be flush with an adjacent surface of the port opening. Without a flush external seal at the port opening when the needleless connector is in a closed position, some fluid may leak from an interior portion of the needleless connector and/or dry or harden within a recess formed at the port opening. Moreover, such a recess, small slit or other penetration from the exterior surface of the port opening caused by a non-flush external seal may trap bacteria or other contamination within a portion of the needleless connector.

SUMMARY

The disclosed subject matter relates to connectors having flexible valves. In certain embodiments, a flexible valve for a connector is described that comprises a head having a top section and a column section defining an axial center of the head, wherein the top section includes a top planar surface that is non-perpendicular with respect to the axial center of the column section; a primary seal portion coupled to the head; and a lower portion coupled to the primary seal portion.

In certain embodiments, a needleless connector is described that comprises a connector housing, the connector housing defining an internal cavity and comprising a port section having a top port surface and a port channel; and a flexible valve disposed within at least a portion of the internal cavity and movably retained within the connector housing, the flexible valve comprising: a head slidably engaged with the port channel of the connector housing, the head comprising a top section and a column section defining an axial center of the head, wherein the top section includes a top planar surface that is non-perpendicular with respect to the axial center of the column section when the flexible valve is not disposed within the connector housing, wherein the top planar surface of the head of the flexible valve has a resulting plane that is substantially perpendicular to the axial center of the column section of the head when the head is engaged with the port channel of the connector housing in a sealed configuration It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIG. 2 is a front plan view illustrating an example of a flexible valve, in accordance with various aspects of the present disclosure.

FIG. 3 is a cross-sectional view illustrating an example of a flexible valve, in accordance with various aspects of the present disclosure.

DETAILED DESCRIPTION

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be apparent to those skilled in the art that the subject technology may be practiced without these specific details. In some examples, like components may be labeled with identical element numbers for ease of understanding.

Figure 1A:
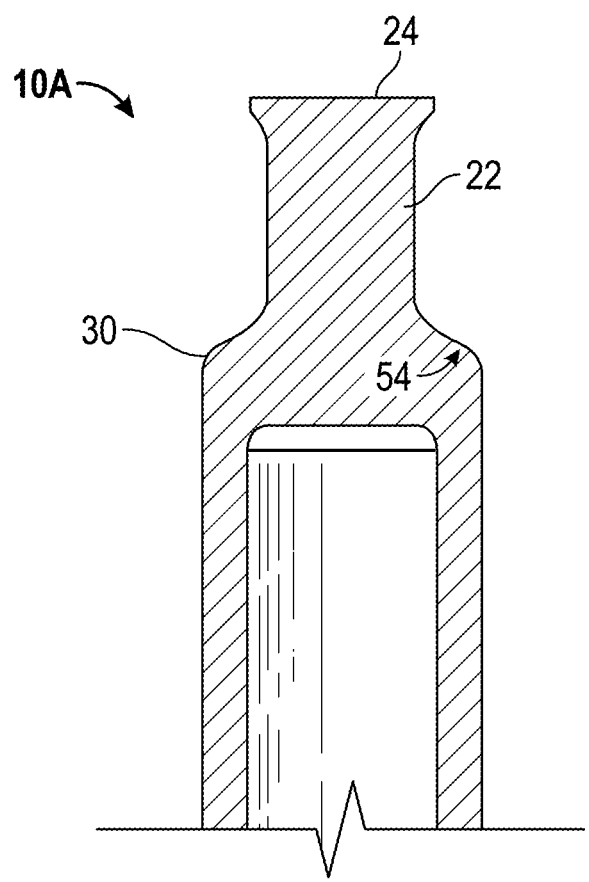
FIGS. 1A, 1B, 1C, and 1D are cross-sectional views illustrating valves and valves employed in connectors.
Figure 1B:
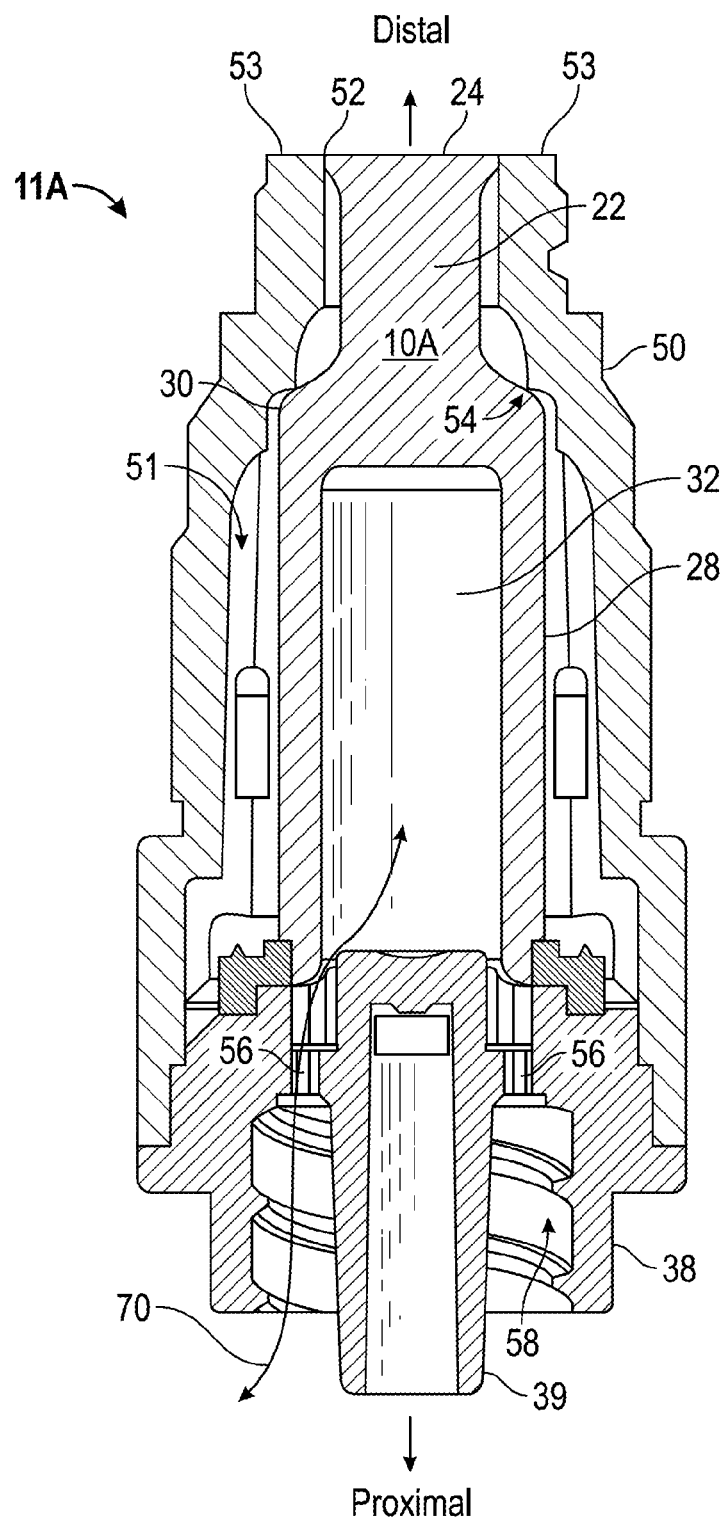

FIG. 1A shows a valve 10a and FIG. 1B shows the valve 10a within a connector 11a. Valve 10a has a solid head 22 and a shoulder 30 that may be used to form a primary seal that blocks the fluid flow path in the connector 11a. A top surface 24 of the head 22 is perpendicular with respect to a longitudinal axis of the head 22 and/or valve 10a in general so that the top surface 24 may be generally flush with an edge surface 53 of a port 52 on the connector 11a. The valve 10a is formed with a perpendicular top surface 24 to align with the edge surface 53 of the port 52 on the connector 11a and present a flat surface at the port 52 when the valve 10a is in a closed position in the connector 11a. The valve 10a includes an internal air space 32 that is generally confined by a cylindrical wall 28. The cylindrical wall 28 of the valve 10a collapses when an axial force is applied to the perpendicular top surface 24.

As shown in FIG. 1B, the connector 11a includes valve 10a disposed within a cavity 51 of body 50. The valve 10a has a shoulder 30 that continuously contacts a ridge 54 within the cavity 51 when the connector 10a is de-activated (i.e., not connected to a mating connector) to form a primary seal that blocks the fluid flow path through the connector 11a. At the same time, the perpendicular top surface 24 of valve 10a is positioned generally flush with the port 52 of the cavity 51 and the edge surface 53, and top surface 24 of valve 10a seals the port 52. A continuous top surface (i.e., edge surface 53 and top surface 24) is intended, and typically provided with a solid-headed valve, such that there is no slit or penetration in the continuous top surface that may trap bacteria or other contamination. The valve 10a has an internal air space 32 that is separated from the cavity 51 by the cylindrical wall 28. The air space 32 is vented to the ambient environment through air passages 56 and the external cavity 58 within the threaded connector 38 surrounding the male luer fitting 39 of the body 50, as indicated by the air flow path 70.

Figure 1C:
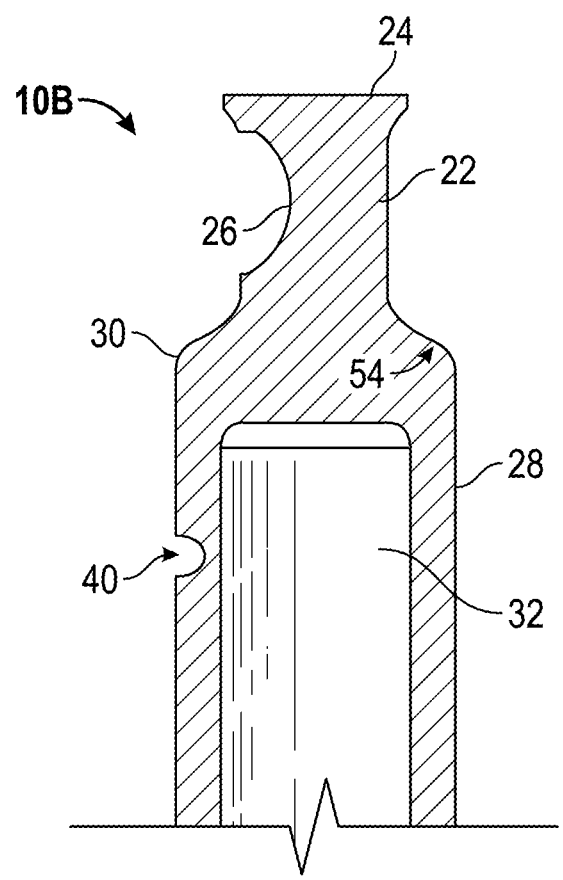
Figure 1D:
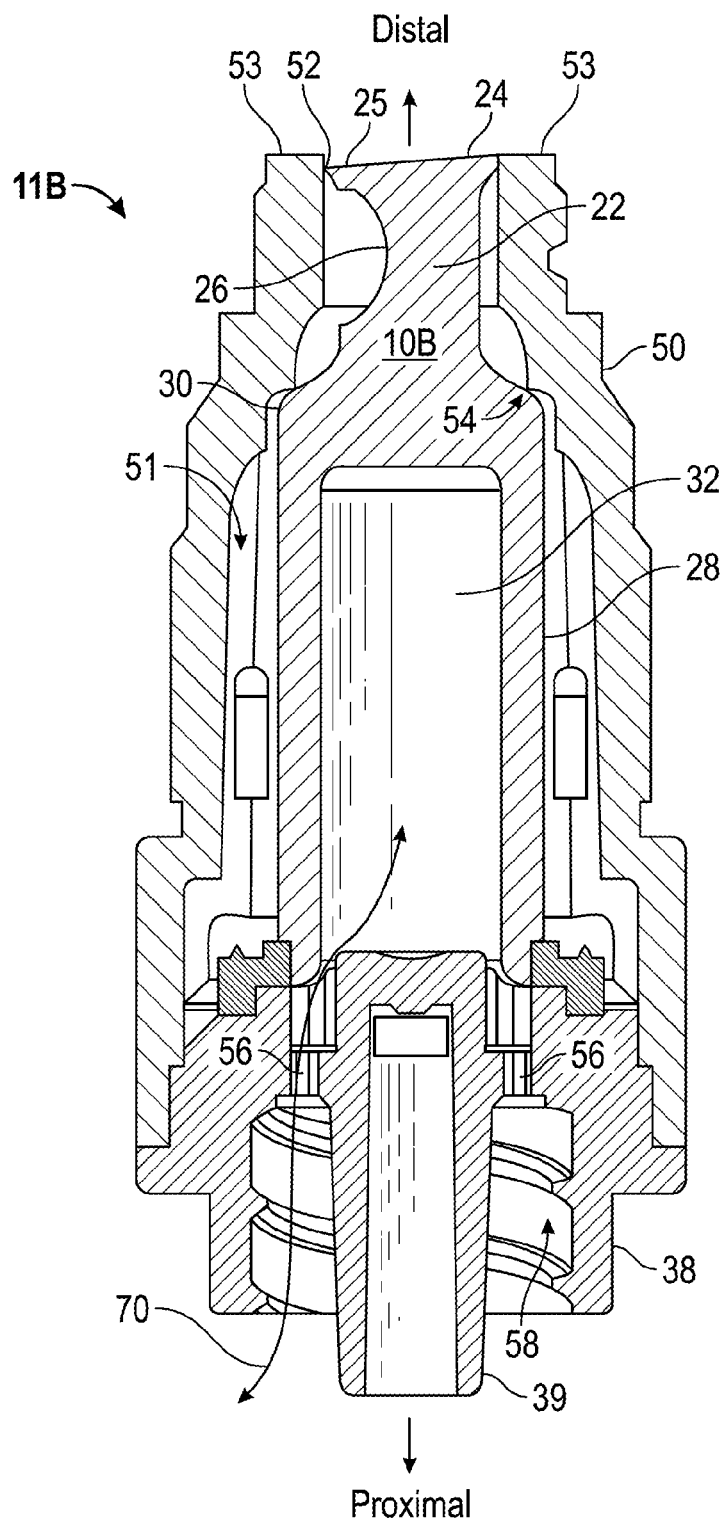

FIG. 1C shows a valve 10b and FIG. 1D shows the valve 10b within a connector 11b. Valve 10b has a cut 26 (e.g., a "smiley cut") formed on one side or portion of the head 22. As with valve 10a, top surface 24 of the head 22 of valve 10b is also perpendicular with respect to a longitudinal axis of the head 22 and/or valve 10b in general so that the top surface 24 may be generally flush with an edge surface 53 of a port 52 on the connector 11b. The valve 10b is formed with a perpendicular top surface 24 with intended to align with the edge surface 53 of the port 52 on the connector 11b and present a flat surface at the port 52 when the valve 10b is in a closed position in the connector 11b.

However, in some instances as shown in FIG. 1D, when the connector 10b is de-activated (i.e., not connected to a mating connector) to form a primary seal that blocks the fluid flow path through the connector 11b, the perpendicular top surface 24 of valve 10b may not be positioned generally flush with the port 52 of the cavity 51 and the edge surface 53. Thus, a continuous top surface (i.e., edge surface 53 and top surface 24) does not result and a recess, slit or penetration 25 in the top surface of connector 11b may trap bacteria or other contamination.

Flexible valves such as, but not limited to, those in FIGS. 1A and 1C can perform multiple complex functions in a needleless connector assembly. For example, various portions of a flexible valve may be utilized for functions and features such as, but not limited to, a sealing mechanism, an actuation arm member for breaking a seal, and/or a resilient spring member for reestablishing a seal. Moreover, various portions of a flexible valve may provide collapsing and canting functions and features for facilitating fluid flow through the needleless connector. In this regard, it is to be appreciated that a balance between rigidity for support and flexibility for movement may be required for certain flexible valves and needleless connectors.

It is to be further appreciated that with smaller needleless connectors and correspondingly smaller flexible valves, the competing needs for both rigidity and flexibility becomes more difficult to balance. Moreover, it is desirable for some needleless connector applications to ensure that there is a flush seal between an exterior-facing portion of the flexible valve and the needleless connector housing at a port of the needleless connector. Without such a flush external seal of the flexible valve and needleless connector housing, some fluid may leak from an interior portion of the needleless connector and harden within a recess formed in the port between the valve and the connector housing (e.g., as described above and illustrated in FIG. 1D). Such a recess, small slit or other penetration at the exterior surface of the port may trap bacteria or other contamination within the needleless connector assembly.

FIGS. 2 and 3 illustrate in isolation an exemplary flexible valve constructed in accordance with embodiments of the present disclosure. Such a valve is used in needleless connectors constructed in accordance with embodiments of the present disclosure. Flexible valve 100 comprises a head 110, a primary seal portion 120, and a lower portion 130. The head 110 has a column section 118 defining an axial center 101 of the flexible valve 100. Axial center 101 extends longitudinally through the head 110 of the flexible valve 100. However, in certain embodiments, the lower portion of the flexible valve 100 does not have the same axial center as the head or other portions of the flexible valve 100. For example, the lower portion of the flexible valve 100 will have no axial center when the lower portion comprises a resilient S-shaped shaft member in certain embodiments.

The head 110 comprises a top section 112 that includes a top surface 116. The top surface 116 has a non-perpendicular plane angle with respect to the axial center 101 of the column section 118. In this regard, the top section 112 of the head 110 is asymmetrical such that the plane of the top surface 116 is at a non-perpendicular angle ($\alpha$) with respect to the axial center 101 in a resting or unutilized state (i.e., prior to construction of the needleless connecter when the flexible valve 100 has not been inserted into a needleless connector housing). The non-perpendicular plane angle ($\alpha$) is between approximately 1° to approximately 30°. In certain embodiments, the non-perpendicular plane angle ($\alpha$) is approximately 3°.

The head 110 of FIGS. 2 and 3 comprises at least one notch 114 disposed along the exterior of the column section 118. The column section 118 of the embodiments of FIGS. 2 and 3 has a generally solid cylindrical section. As can be seen with respect to the longitudinal cross-sectional view of FIG. 3, the at least one notch 114 comprises an arcuate-shaped recess within the column section 118. However, it is to be appreciated that the implementations of the notch 114 may comprise a variety of shapes and sizes, such as, but not limited to, notches having triangular or various geometric cross-sections.

In certain embodiments, the head of the flexible valve does not include a notch, but rather has a discontinuity segment disposed on the column section. For example, one side or a portion of one side of the column section may be comprised of a different material (or a same material with a different hardness value) than the remainder of the column section. Additionally, one side or a portion of one side of the column section may be hollow, while the other side or portion of the remainder of the column section may be solid. Thus, an effective change in the resiliency with respect to the movement of the head (similar to that of a removed or extracted volume of a notch) may result.

Referring again to FIGS. 2 and 3, the primary seal portion 120 includes a cross-section area greater than a cross-section area of the column section of the head 110. For example, the primary seal portion 120 comprises a frustoconical surface 122 for engaging with an internal sealing edge of a connector housing. The frustoconical shape of the primary seal portion 120 is configured such that a first cross-sectional area of the primary seal portion 120 proximal the head 110 is smaller than a second cross-sectional area of the primary seal portion 120 distal the head 110. In other words, the primary seal portion 120 is narrower towards the head 110 and wider towards the lower portion 130

Lower portion 130 comprises an elongated tubular member 131 having a closed end 136 proximal the primary seal portion 120 and an open end 138 distal the primary seal portion 120. A wall 132 of the lower portion 130 may define, in part, an interior air space 134 of the flexible valve 100. According to some aspects, the flexible valve 100 is collapsible in operation with a needleless connector assembly.

In this regard, the lower portion 130 comprises various dimples and/or incisions to facilitate proper collapsing functionality in accordance with different embodiments of the present disclosure. Moreover, while the head 110 of the valve 110 may comprise generally cylindrical properties allowing it to operate with a male luer-tapered tip of a medical implement or similar interconnection device, the lower portion 130 may comprise a plurality of shapes, sizes, and characteristics associated with the functionality and operation of the flexible valve in conjunction with the needleless connector apparatus in which it is used. In some aspects, when the lower portion 130 comprises a tubular section 131, this section 131 may comprise a plurality tubular shapes, such as, but not limited to, cylindrical, rectangular, hexagonal, tubular shapes.

Figure 5:
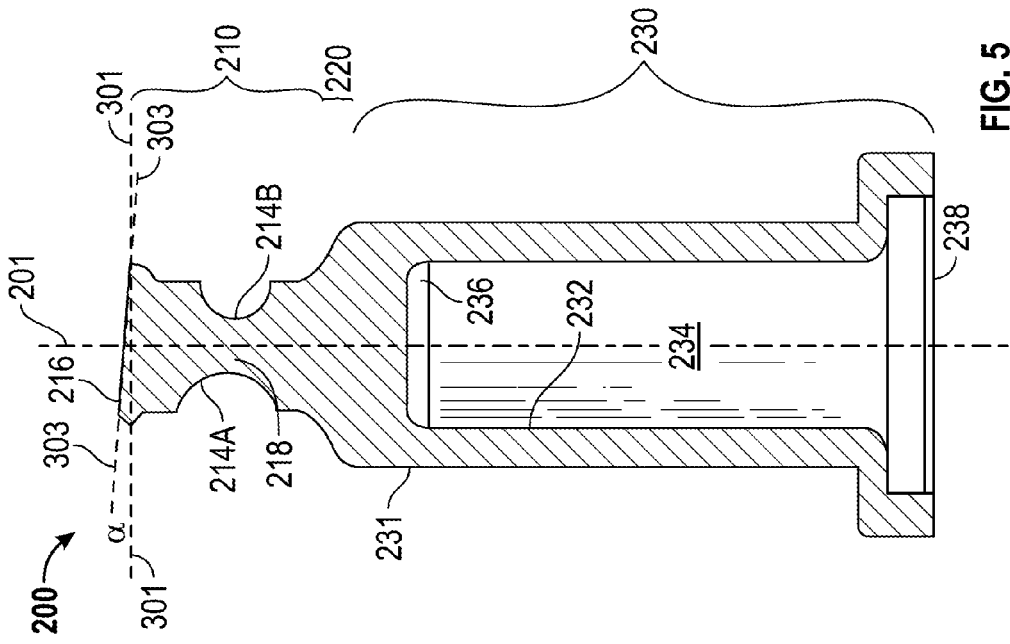
FIG. 5 is a cross-sectional view illustrating an example of a flexible valve, in accordance with various aspects of the present disclosure.
Figure 4:
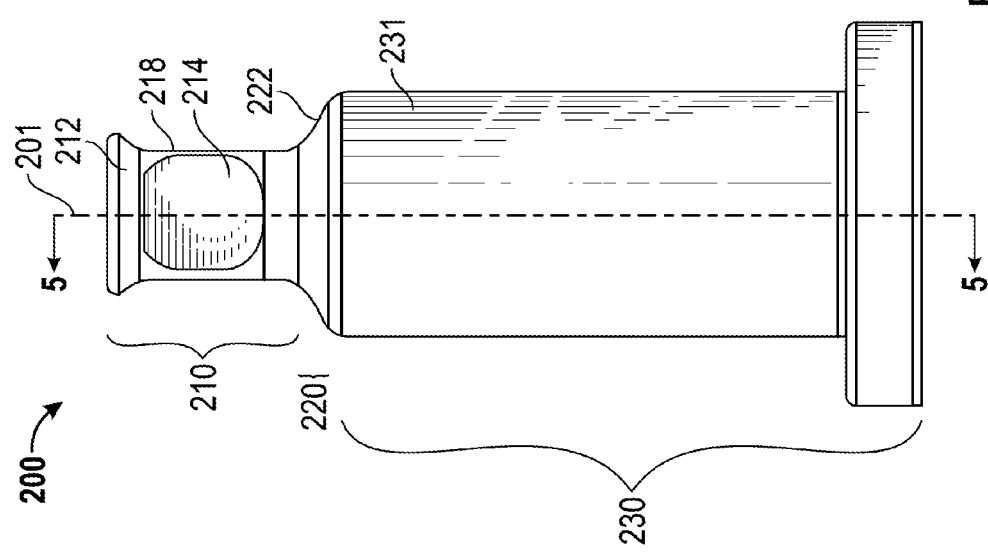
FIG. 4 is a front plan view illustrating an example of a flexible valve, in accordance with various aspects of the present disclosure.

FIGS. 4 and 5 illustrate a flexible valve 200 constructed in accordance with other embodiments of the present disclosure. These embodiments are the same as those shown in FIGS. 2 and 3, except that notches 214a and 214b, respectively, are provided in the head 210.

As can be seen with respect to the longitudinal cross-sectional view of FIG. 5, a first notch 214a and a second notch 214b each comprises an arcuate-shaped recess from the column section 218 in accordance with certain embodiments. As discussed above with respect to the flexible valve 100, implementations of the notch may comprise a variety of shapes and sizes, such as, but not limited to, those having triangular or various geometric cross-sections.

In an aspect, the head of the flexible valve may not include first and second notches (or any plurality of notches), but rather have first and second discontinuity segments disposed on the column section. Thus, a change in the resiliency that affects the movement of the head can result.

Figure 6:
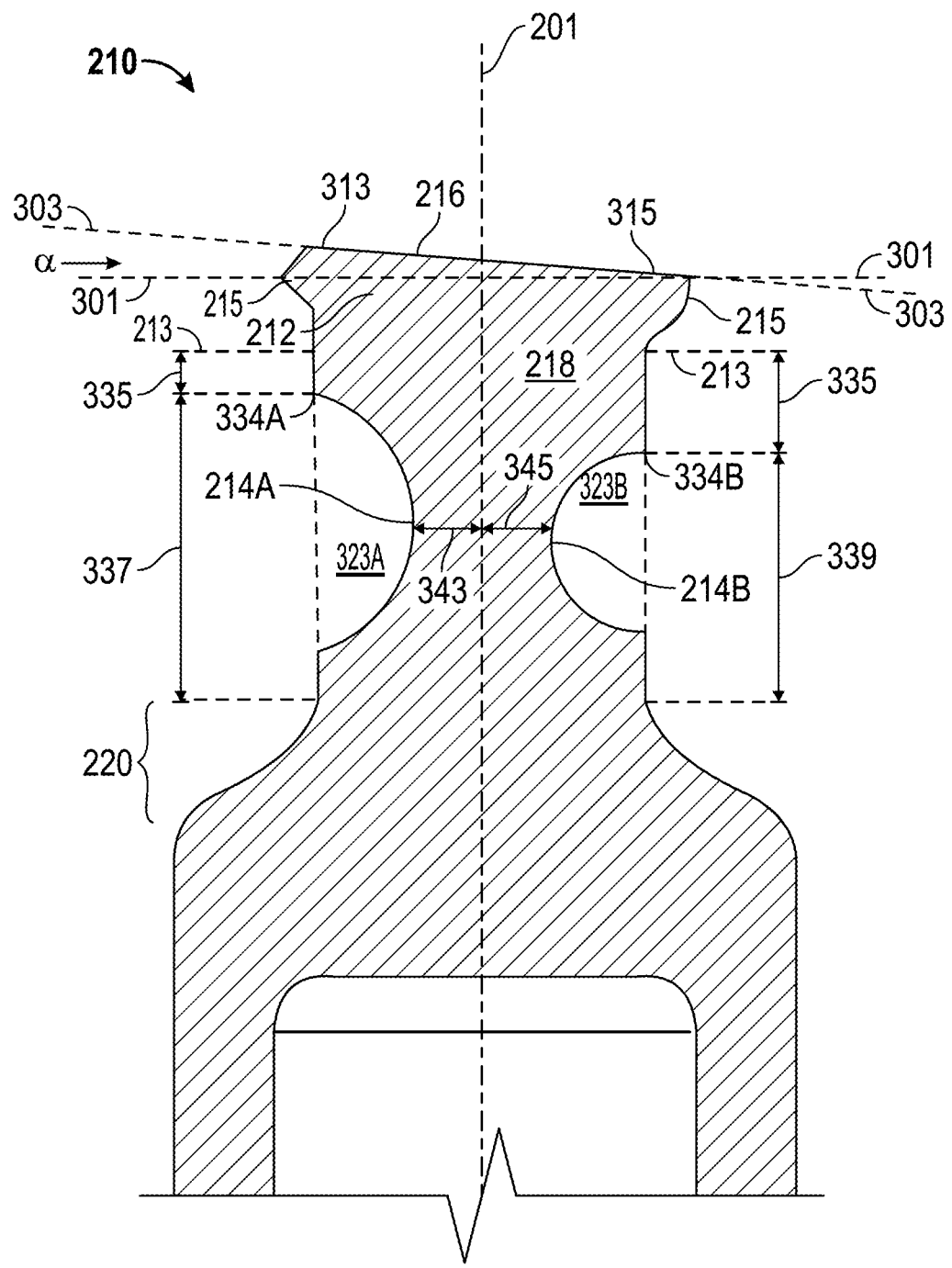
FIG. 6 is a partial cross-sectional view illustrating an example of a head of a flexible valve, in accordance with various aspects of the present disclosure.

Referring to FIG. 6, a partial and enlarged cross-sectional view of the head 210 of flexible valve 200 is shown. In certain embodiments, a non-perpendicular plane 303 of the top surface 216 has a non-perpendicular plane angle (α). In some embodiments, the top section 112 of the head 210 also includes a circumferential lip 215 or similar protrusion therearound for slidably and sealably engaging with a port channel (see, e.g., port channel 456 FIG. 7) of a needleless connector housing. In an aspect, a perpendicular cross-section 301 of the top portion 212 may be defined at an intersection point of the axial center 201 with the top surface 216. Thus, a portion 313 of the top surface 212 may be defined as being above the perpendicular cross-section 301 of the head 210, and a portion 315 of the top surface 212 may be defined as being below the perpendicular cross-section 301. The perpendicular cross-section 301 may be used as a reference plane and is perpendicular with respect to the axial center 201 of the column section 218.

In certain embodiments, the first notch 214a has a greater volume 323a than the second notch 214b. As shown in the cross-sectional view of FIG. 6, the volume 323b of the second notch 214b is less than the volume 323a of the first notch 214a. Thus, a non-perpendicular plane 303 may be defined such that the portion 313 of the top surface 212 above a perpendicular cross-section 301 is disposed above the first notch 214a.

In an aspect, the first notch 214a may have a top edge 334a closer to a bottom edge 213 of the top section 212 (or farther 337 from the primary seal portion 220), than the second notch 214b. As shown in the cross-sectional view of FIG. 6, a distance 335 between the top edge 334b of the second notch 214b is farther from the bottom edge 213 of the top section 212 (or closer 339 to the primary seal portion 220) than the distance 333 of the first notch 214a. Thus, the non-perpendicular plane 303 may be defined such that a portion 313 of the top surface 212 above a perpendicular cross-section 301 is disposed above the first notch 214a.

Still referring to FIG. 6, in an aspect, the first notch 214a may extend closer to the axial center 201 (with reference to the deepest point of the first notch 214a into the column section 218) than the second notch 214b. As shown in the cross-sectional view of FIG. 6, a distance 345 between the deepest point of the second notch 214b and the axial center 201 is farther than a distance 343 between the deepest point of the first notch 214a and the axial center 201. Thus, the non-perpendicular plane 303 may be defined such that a portion 313 of the top surface 212 above a perpendicular cross-section 301 is disposed above the first notch 214a.

It is to be understood that while the first notch 214a and second notch 214b are shown generally opposite each other on the column section 218, other arrangements of the at least one notch on the column section, including three or more notches, are contemplated.

Embodiments of the flexible valve 100, 200 may comprise any of the various materials used for producing mechanical valves for needleless connectors and other medical implements. In some implementations, the head 110, 210 may comprise of an elastomeric material, such as but not limited to, a silicone compound. Moreover, the primary seal portion 120, 220 and lower portion 130, 230 may comprise an elastomeric material. For example, in some implementations, the head 110, 210 and primary seal portion 120, 220 may have a durometer value of approximately 70 on a Shore A hardness scale. In certain implementations, all or some of the flexible valve may be comprised of liquid silicone rubbers of the Wacker ELASTOSIL® LR 3003 Series having a Shore A hardness durometer value of 70.

Additionally, according to certain embodiments, the elastomeric material of the head may have a higher durometer value than the elastomeric material of the lower portion. For example, the collapsing functionality of the lower portion associated with facilitating a fluid flow path in the needleless connector may benefit from a more pliable material or composition attributes for operation, whereas the head and primary seal portion may require a more rigid construction for disengaging the primary seal.

Figure 7:
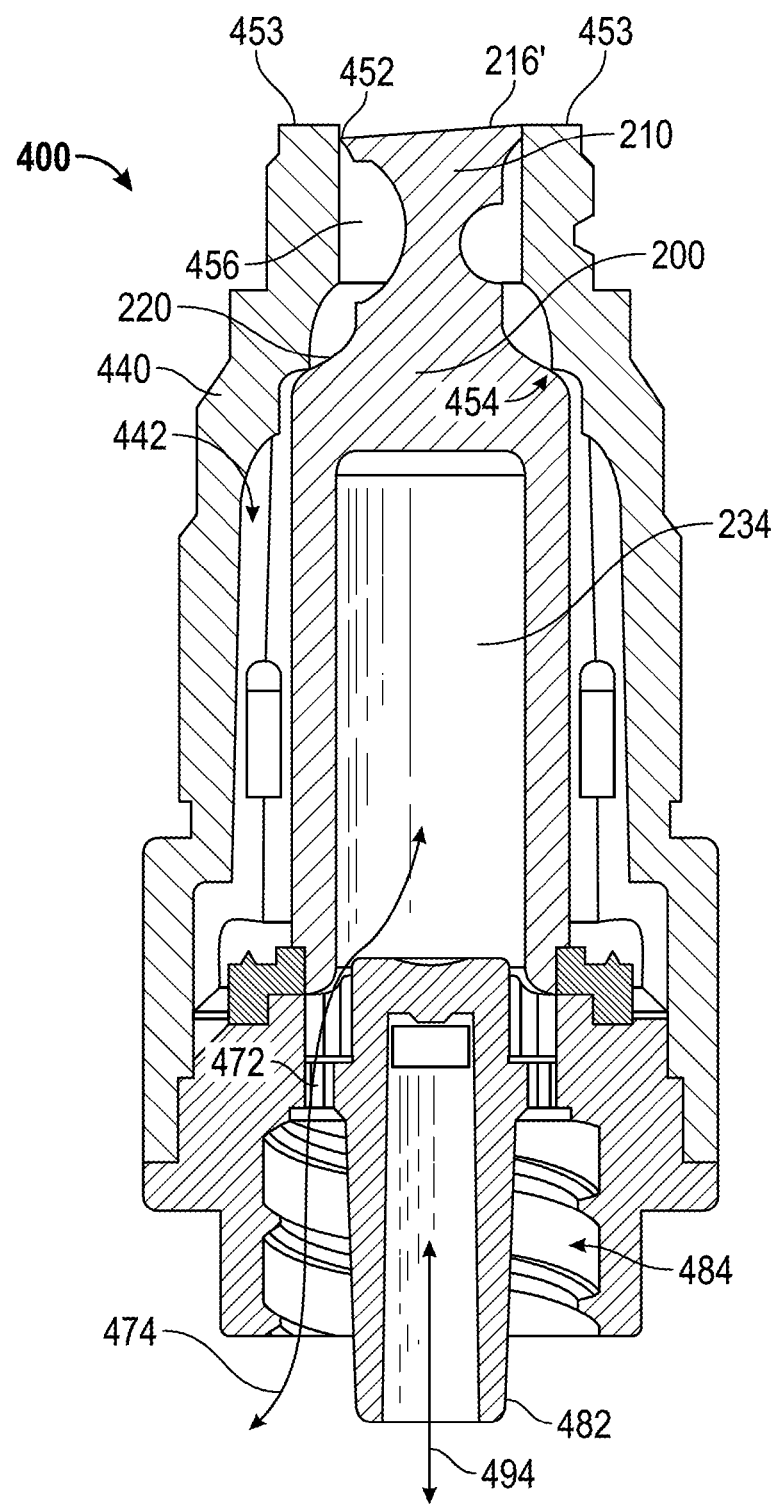
FIG. 7 is a cross-sectional view illustrating an example of a needleless connector assembly, in accordance with various aspects of the present disclosure.

FIG. 7 illustrates an example of a needleless connector assembly comprising a flexible valve 200, although flexible valve 100 can be substituted for flexible valve 200 in certain embodiments. Needleless connector assembly 400 comprises a connector housing 440 and the flexible valve 200, for example. The connector housing 440 defines an internal cavity 442 and comprises a port section 452 having a top port surface 454 and a port channel 456. The connector housing 440 also comprises an internal sealing edge 454.

The flexible valve 200 is disposed within at least a portion of the internal cavity 442 and is movably retained within the connector housing 440. In this regard, the internal sealing edge 454 is configured such that the flexible valve 200 is movable to facilitate fluid flow (e.g., inserting a male luer-tapered tip of a medical implement into the port channel 456), but will spring back and engage with the internal sealing edge 454. The flexible valve 200 is retained within the connector housing 440 at least in part by the internal sealing edge 454.

The head 210 of the flexible valve 200 is slidably engaged with the port channel 456 of the connector housing 440, and the primary seal portion 220 is removably engaged with the internal sealing edge 454 of the connector housing 440.

In certain embodiments, the top surface 216' of the head 210 of the flexible valve 200 has a resulting plane that is substantially perpendicular to the axial center of the column section 218 of the head 210 when the head 210 is engaged with the port channel 456 of the connector housing 440 in a sealed configuration.

Still referring to FIG. 7, the needleless connector 400 may be in a sealed configuration (or closed state) when a primary seal is formed by contact between the primary seal portion 220 of the flexible valve 200 and the internal sealing edge 454 of the connector housing 440. In the sealed configuration, the port channel 456 of needleless connector 400 is not in receipt of a male luer-tapered tip or other medical implement for fluid engagement therewith. The needleless connector 400 may be changed to an unsealed configuration (or opened state) when the primary seal between the internal sealing edge 454 of the connector housing 440 and the primary seal portion 220 of the flexible valve 200 is temporarily broken or separated when a male luer-tapered tip or other medical implement is inserted into the port channel 456 of the connector housing 440.

In certain embodiments, the top surface 216' of the head 210 of the flexible valve 200 is substantially flush with the top port surface 453 of the connector housing 440 when the head 210 is engaged with the port channel 456 of the connector housing 440 in the sealed configuration.

In operation, an air passage channel 472 may facilitate an air flow path 474 from an internal air space of the flexible valve 200 and an interconnected device. Connector housing 440 may further comprise a male luer-taper fitting 482 and threaded connector 484 for medical device implement interconnection. A fluid pathway may be provided through the male luer-taper fitting 482 of the needleless connector 400.

Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. For example, in some aspects, certain elements of the flexible valve when coupled may be fixably attached. Similarly, in some aspects, certain elements of the connector housing when coupled may be fixably attached. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology.

The disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. §101, 102, or 103, nor should they be interpreted in such a way.

What is claimed is:

1. A flexible valve for a connector, comprising:
a head having a top section, a column section having an outer circumferential surface and defining an axial center of the head, and at least one discontinuity disposed on the column section such that the at least one discontinuity does not include at least a portion of the outer circumferential surface with respect to a cross-sectional plane perpendicular to axial center, wherein the top section includes a top planar surface that is non-perpendicular with respect to the axial center;
a primary seal portion coupled to the head; and
a lower portion coupled to the primary seal portion.

2. The flexible valve of claim 1, wherein the discontinuity comprises at least one discontinuity segment disposed on the column section, and wherein a non-perpendicular angle of the top planar surface is defined based on an attribute of the at least one discontinuity.

3. The flexible valve of claim 1, wherein the at least one discontinuity comprises at least one notch disposed on the column section, and wherein a non-perpendicular angle of the top planar surface is defined such that a portion of the top planar surface above a perpendicular cross-section is disposed above the at least one notch.

4. The flexible valve of claim 3, wherein the at least one notch comprises a first notch and a second notch.

5. The flexible valve of claim 4, wherein the first notch has a greater recess volume from the column section than the second notch, and wherein the non-perpendicular angle is defined such that a portion of the top planar surface above a perpendicular cross-section is disposed above the first notch.

6. The flexible valve of claim 4, wherein the first notch has a top edge closer to the top section than a top edge of the second notch, and wherein the non-perpendicular angle of the top planar surface is defined such that a portion of the top planar surface above a perpendicular cross-section is disposed above the first notch.

7. The flexible valve of claim 4, wherein the first notch extends closer to the axial center than the second notch, and wherein the non-perpendicular angle of the top planar surface is defined such that a portion of the top planar surface above a perpendicular cross-section is disposed above the first notch.

8. The flexible valve of claim 1, wherein a non-perpendicular angle of the top planar surface is defined such that a resulting plane of the top planar surface is substantially perpendicular to the axial center when the head is engaged with a port channel of a connector housing in a sealed configuration.

9. The flexible valve of claim 1, wherein the head comprises an elastomeric material.

10. The flexible valve of claim 9, wherein the elastomeric material of the head comprises a silicone compound.

11. The flexible valve of claim 9, wherein the primary seal portion and lower portion comprise an elastomeric material.

12. The flexible valve of claim 11, wherein the elastomeric material of the head has a higher durometer value than the elastomeric material of the lower portion.

13. The flexible valve of claim 1, wherein the primary seal portion includes a cross-section area greater than a cross-section area of the column section of the head.

14. The flexible valve of claim 1, wherein the lower portion comprises an elongated tubular member having a closed end proximal to the primary seal portion and an open end distal to the primary seal portion.

15. A needleless connector assembly comprising:
a connector housing, the connector housing defining an internal cavity and comprising a port section having a top port surface and a port channel; and
a flexible valve disposed within at least a portion of the internal cavity and movably retained within the connector housing, the flexible valve comprising:
a head slidably engaged with the port channel of the connector housing, the head comprising a top section and a column section defining an axial center of the head, wherein the top section includes a top planar surface that is non-perpendicular with respect to the axial center of the column section when the flexible valve is not disposed within the connector housing,
wherein the top planar surface of the head of the flexible valve has a resulting plane that is substantially perpendicular to the axial center of the column section of the head when the head is engaged with the port channel of the connector housing in a sealed configuration.

16. The needleless connector assembly of claim 15, wherein the top planar surface of the head of the flexible valve is substantially flush with the top port surface of the connector housing when the head is engaged with the port channel of the connector housing in the sealed configuration.

17. The needleless connector assembly of claim 15, wherein the flexible valve further comprises:
a primary seal portion removably engaged with an internal sealing edge of the connector housing, the primary seal portion being coupled to the head; and
a lower portion, the lower portion being coupled to the primary seal portion.

18. A flexible valve for a connector, comprising:
a head having a top section, a column section defining an axial center of the head, a first notch disposed on the column section, and a second notch disposed on the column section, wherein the top section includes a top planar surface that is non-perpendicular with respect to the axial center;
a primary seal portion coupled to the head; and
a lower portion coupled to the primary seal portion,
wherein a non-perpendicular angle of the top planar surface is defined such that a portion of the top planar surface above a perpendicular cross-section is disposed above at least one of the first notch or the second notch.

19. A flexible valve for a connector, comprising:
a head having a top section and a column section defining an axial center of the head, wherein the top section includes a top planar surface that is non-perpendicular with respect to the axial center;
a primary seal portion coupled to the head; and
a lower portion coupled to the primary seal portion,
wherein the head comprises an elastomeric material,
wherein the primary seal portion and lower portion comprise an elastomeric material, and
wherein the elastomeric material of the head has a higher durometer value than the elastomeric material of the lower portion.

20. A flexible valve for a connector, comprising:
a head having a top section and a column section defining an axial center of the head, wherein the top section includes a top planar surface that is non-perpendicular with respect to the axial center;
a primary seal portion coupled to the head; and
a lower portion coupled to the primary seal portion,
wherein the lower portion comprises an elongated tubular member having a closed end proximal to the primary seal portion and an open end distal to the primary seal portion.

* * * * *